United States Patent
Purves

(10) Patent No.: US 10,925,515 B2
(45) Date of Patent: Feb. 23, 2021

(54) ALVEOLAR BREATH COLLECTION APPARATUS

(71) Applicant: Picomole Inc., Moncton (CA)

(72) Inventor: Chris Purves, Moncton (CA)

(73) Assignee: PICOMOLE INC., Moncton (CA)

(*) Notice: Subject to any disclaimer, the term of this patent is extended or adjusted under 35 U.S.C. 154(b) by 141 days.

(21) Appl. No.: 15/917,225

(22) Filed: Mar. 9, 2018

(65) Prior Publication Data

US 2018/0214050 A1 Aug. 2, 2018

Related U.S. Application Data

(63) Continuation-in-part of application No. 14/720,456, filed on May 22, 2015, now Pat. No. 9,918,661.
(Continued)

(51) Int. Cl.
*A61B 5/08* (2006.01)
*A61B 5/083* (2006.01)
(Continued)

(52) U.S. Cl.
CPC ............ *A61B 5/0836* (2013.01); *A61B 5/097* (2013.01); *G01N 33/004* (2013.01);
(Continued)

(58) Field of Classification Search
CPC ....... A61B 5/0836; A61B 5/097; A61B 5/082; A61B 2010/0087; G01N 33/004; G01N 33/0047; Y02A 50/249
See application file for complete search history.

(56) References Cited

U.S. PATENT DOCUMENTS 3,517,330 A 6/1970 Doyle et al.
4,410,271 A 10/1983 Matthews
(Continued)

FOREIGN PATENT DOCUMENTS

CA 2792032 A1 9/2011
CA 2997070 A1 9/2019
(Continued)

OTHER PUBLICATIONS

Cope et al. Effects of ventilation on the collection of exhaled breath in humans:, J App I Physiol 96: 1371-1379, 2004. 2004.
(Continued)

*Primary Examiner* — Navin Natnithithadha
*Assistant Examiner* — Andrey Shostak
(74) *Attorney, Agent, or Firm* — Millman IP Inc.

(57) ABSTRACT

An apparatus for collecting volatile organic compounds from a gas sample such as alveolar breath or room air comprises an exhaust portion having at least a flow measuring device, and a discriminating device for distinguishing between alveolar and non-alveolar breath. The apparatus further comprises a collection portion distinct from and parallel with the exhaust portion having at least a collection component for receiving and concentrating gas samples within a collection chamber and a sampling component having a plurality of sampling devices for receiving the concentrated gas sample from the collection chamber and isolating VOCs contained in the gas sample. The collection chamber is compressible via a drive mechanism for precisely actuating the chamber to draw a gas sample into the collection chamber and circulating the sample to the sampling devices. Use of a drive mechanism enables the exhaust portion to be distinct from the collection portion, thereby mitigating cross-contamination therebetween.

9 Claims, 7 Drawing Sheets

Related U.S. Application Data

(60) Provisional application No. 62/002,159, filed on May 22, 2014.

(51) Int. Cl.
*A61B 5/097* (2006.01)
*G01N 33/00* (2006.01)
*A61B 10/00* (2006.01)

(52) U.S. Cl.
CPC .......... *G01N 33/0047* (2013.01); *A61B 5/082* (2013.01); *A61B 2010/0087* (2013.01); *Y02A 50/20* (2018.01)

(56) References Cited

U.S. PATENT DOCUMENTS

| | | | |
|---|---|---|---|
| 4,468,773 A | 8/1984 | Seaton | |
| 4,648,714 A | 3/1987 | Benner et al. | |
| 4,672,618 A | 6/1987 | Wijntjes et al. | |
| 4,779,279 A | 10/1988 | Brown | |
| 4,784,486 A | 11/1988 | Van Wagenen et al. | |
| 4,964,132 A | 10/1990 | Fischer | |
| 5,014,278 A | 5/1991 | Deki | |
| 5,029,174 A | 7/1991 | Anderson et al. | |
| 5,091,912 A | 2/1992 | Bretenaker et al. | |
| 5,135,304 A | 8/1992 | Miles et al. | |
| 5,465,728 A | 11/1995 | Phillips | |
| 5,528,040 A | 6/1996 | Lehmann | |
| 5,573,005 A * | 11/1996 | Ueda ................... | A61B 5/083 422/84 |
| 5,646,952 A | 7/1997 | Whittley | |
| 5,815,277 A | 9/1998 | Zare et al. | |
| 5,903,358 A | 5/1999 | Zare et al. | |
| 5,912,740 A | 6/1999 | Zare et al. | |
| 6,076,392 A | 6/2000 | Drzewiecki | |
| 6,084,682 A | 7/2000 | Zare et al. | |
| 6,233,052 B1 | 5/2001 | Zare et al. | |
| 6,324,191 B1 | 11/2001 | Horvath | |
| 6,363,772 B1 | 4/2002 | Berry | |
| 6,466,322 B1 | 10/2002 | Paldus et al. | |
| 6,479,019 B1 | 11/2002 | Goldstein et al. | |
| 6,504,145 B1 | 1/2003 | Romanini et al. | |
| 6,540,691 B1 | 4/2003 | Phillips | |
| 6,563,583 B2 | 5/2003 | Ortyn et al. | |
| 6,582,376 B2 | 6/2003 | Baghdassarian | |
| 6,726,637 B2 | 4/2004 | Phillips | |
| 6,727,492 B1 | 4/2004 | Ye et al. | |
| 6,865,198 B2 | 3/2005 | Taubman | |
| 6,952,945 B2 | 10/2005 | O'Brien | |
| 7,004,909 B1 | 2/2006 | Patel et al. | |
| 7,012,696 B2 | 3/2006 | Orr et al. | |
| 7,101,340 B1 | 9/2006 | Braun | |
| 7,106,763 B2 | 9/2006 | Tan et al. | |
| 7,235,054 B2 | 6/2007 | Eckerbom | |
| 7,352,463 B2 | 4/2008 | Bounaix | |
| 7,391,517 B2 | 6/2008 | Trebbia et al. | |
| 7,450,240 B2 | 11/2008 | Morville et al. | |
| 7,541,586 B2 | 6/2009 | Miller | |
| 7,555,024 B2 | 6/2009 | Ishaaya et al. | |
| 7,569,823 B2 | 8/2009 | Miller | |
| 7,606,274 B2 | 10/2009 | Mirov et al. | |
| 7,612,885 B2 | 11/2009 | Cole et al. | |
| 7,613,216 B2 | 11/2009 | Nakagawa | |
| 7,616,123 B2 | 11/2009 | Ridder et al. | |
| 7,646,485 B2 | 1/2010 | Tan | |
| 7,679,750 B2 | 3/2010 | Li et al. | |
| 7,902,534 B2 | 3/2011 | Cole et al. | |
| 8,018,981 B2 | 9/2011 | Eckles et al. | |
| 8,288,727 B2 | 10/2012 | Cormier et al. | |
| 8,659,758 B2 | 2/2014 | Koulikov et al. | |
| 8,659,759 B2 | 2/2014 | Koulikov et al. | |
| 8,665,442 B2 | 3/2014 | Koulikov et al. | |
| 8,885,167 B2 | 11/2014 | Koulikov et al. | |
| 8,982,352 B1 | 3/2015 | Hoffnagle et al. | |
| 9,014,221 B2 | 4/2015 | Kub et al. | |
| 9,097,583 B2 | 8/2015 | Gupta et al. | |
| 9,194,742 B2 | 11/2015 | Kachanov et al. | |
| 9,212,990 B1 | 12/2015 | Muraviev | |
| 9,568,465 B2 | 2/2017 | Rihani et al. | |
| 9,625,702 B2 | 4/2017 | Hodges et al. | |
| 9,671,332 B2 | 6/2017 | Christensen | |
| 9,778,110 B1 | 10/2017 | Rella et al. | |
| 9,918,661 B2 | 3/2018 | Cormier et al. | |
| 10,034,621 B2 | 7/2018 | Wondka et al. | |
| 10,130,284 B2 | 11/2018 | Johnson | |
| 10,139,392 B2 | 11/2018 | Kaariainen et al. | |
| 10,168,275 B2 | 1/2019 | Orcutt | |
| 10,194,833 B2 | 2/2019 | Cormier | |
| 10,234,381 B2 | 3/2019 | Koulikov | |
| 10,330,592 B2 | 6/2019 | Koulikov | |
| 10,401,281 B2 | 9/2019 | Koulikov | |
| 10,499,819 B2 | 12/2019 | Wondka et al. | |
| 10,527,492 B2 | 1/2020 | Bouzid | |
| 2003/0109794 A1* | 6/2003 | Phillips ................... | A61B 5/097 600/543 |
| 2004/0022281 A1 | 2/2004 | Steffens et al. | |
| 2004/0137637 A1 | 7/2004 | Wang et al. | |
| 2004/0142484 A1 | 7/2004 | Berlin et al. | |
| 2004/0162500 A1 | 8/2004 | Kline | |
| 2004/0190563 A1 | 9/2004 | Gendron | |
| 2005/0134836 A1 | 6/2005 | Paldus et al. | |
| 2005/0177056 A1* | 8/2005 | Giron .................... | A61B 5/097 600/543 |
| 2005/0177057 A1 | 8/2005 | Friedman et al. | |
| 2005/0201428 A1 | 9/2005 | Cotteverte et al. | |
| 2006/0200037 A1 | 9/2006 | Falasco | |
| 2007/0062255 A1 | 3/2007 | Talton | |
| 2007/0091941 A1 | 4/2007 | Mori et al. | |
| 2007/0133001 A1 | 6/2007 | Cox et al. | |
| 2008/0091085 A1 | 4/2008 | Urushihata et al. | |
| 2008/0139021 A1 | 6/2008 | Suzuki et al. | |
| 2008/0170597 A1 | 7/2008 | van der Veer | |
| 2009/0201957 A1 | 8/2009 | Brotherton-Ratcliffe | |
| 2009/0306527 A1 | 12/2009 | Kubo et al. | |
| 2010/0002234 A1 | 1/2010 | Cormier et al. | |
| 2010/0074089 A1 | 3/2010 | Smith et al. | |
| 2011/0072887 A1* | 3/2011 | Oki ....................... | B03C 3/014 73/28.02 |
| 2011/0216311 A1 | 9/2011 | Kachanov et al. | |
| 2011/0269632 A1 | 11/2011 | Haick | |
| 2011/0295140 A1 | 12/2011 | Zaidi et al. | |
| 2012/0143805 A1 | 6/2012 | Gold et al. | |
| 2012/0250706 A1 | 10/2012 | Stiens et al. | |
| 2012/0266883 A1 | 10/2012 | Taylor et al. | |
| 2012/0309048 A1 | 12/2012 | Ratcliffe et al. | |
| 2013/0144561 A1 | 6/2013 | Harb et al. | |
| 2013/0303929 A1* | 11/2013 | Martino ................. | A61B 5/097 600/532 |
| 2014/0162500 A1 | 6/2014 | Heine | |
| 2014/0293283 A1 | 10/2014 | Farooq et al. | |
| 2014/0320856 A1 | 10/2014 | McKeever et al. | |
| 2015/0032019 A1 | 1/2015 | Acker et al. | |
| 2015/0335267 A1 | 11/2015 | Cormier et al. | |
| 2016/0174875 A1* | 6/2016 | Forster .................. | A61B 10/00 600/543 |
| 2016/0285236 A1 | 9/2016 | Yvind | |
| 2017/0074857 A1* | 3/2017 | Dennis .................. | A61B 5/0836 |
| 2018/0059003 A1 | 3/2018 | Jourdainne | |
| 2018/0156718 A1 | 6/2018 | Fleisher et al. | |
| 2018/0202918 A1 | 7/2018 | Tanaka et al. | |
| 2018/0202923 A1 | 7/2018 | Kageyama et al. | |
| 2018/0214050 A1 | 8/2018 | Purves | |
| 2018/0261974 A1 | 9/2018 | Purves et al. | |
| 2019/0265159 A1 | 8/2019 | Koulikov | |
| 2019/0265160 A1 | 8/2019 | Koulikov | |
| 2019/0271641 A1 | 9/2019 | Koulikov | |
| 2019/0301933 A1 | 10/2019 | Allison | |
| 2019/0323955 A1 | 10/2019 | Koulikov | |

FOREIGN PATENT DOCUMENTS

| | | |
|---|---|---|
| CN | 101470072 A | 7/2009 |
| CN | 102316801 B | 1/2012 |

(56) References Cited

FOREIGN PATENT DOCUMENTS

| | | |
|---|---|---|
| CN | 102798631 A | 11/2012 |
| CN | 102841082 A | 12/2012 |
| CN | 102264292 B | 5/2014 |
| CN | 106908389 A | 6/2017 |
| CN | 107037003 A | 8/2017 |
| CN | 109856054 A | 6/2019 |
| DE | 2130331 A1 | 3/1977 |
| DE | 2723939 A1 | 12/1978 |
| DE | 3819687 A1 | 12/1989 |
| DE | 10156149 A1 | 6/2003 |
| DE | 102013215640 | 2/2015 |
| EP | 557658 A1 | 9/1993 |
| EP | 600711 A2 | 6/1994 |
| EP | 1535047 B1 | 6/2005 |
| EP | 1304955 B1 | 12/2008 |
| EP | 1997198 B1 | 6/2012 |
| EP | 1418842 B1 | 7/2012 |
| EP | 3037805 A1 | 6/2016 |
| EP | 2745097 B1 | 2/2018 |
| EP | 3419122 A1 | 12/2018 |
| EP | 3467473 A1 | 4/2019 |
| GB | 1019295 A | 2/1966 |
| JP | 2001194299 A | 7/2001 |
| JP | 2006189392 A | 7/2006 |
| JP | 2006226727 A | 8/2006 |
| JP | 2010243270 A | 10/2010 |
| JP | 2013011620 A | 1/2013 |
| JP | 5341519 B2 | 11/2013 |
| JP | 5537174 B2 | 7/2014 |
| JP | 2016503904 A | 2/2016 |
| WO | 2090935 | 11/2002 |
| WO | 2005038436 A2 | 4/2005 |
| WO | 2005076875 A2 | 8/2005 |
| WO | 2005088274 A1 | 9/2005 |
| WO | 2017142644 A1 | 12/2007 |
| WO | 2011117572 A1 | 9/2011 |
| WO | 2012004794 A1 | 1/2012 |
| WO | 2014070952 A1 | 5/2014 |
| WO | 2018142027 A1 | 8/2018 |
| WO | 2019239827 A1 | 12/2019 |

OTHER PUBLICATIONS

Orr et al. "Cavity ringdown spectroscopy with widely tunable swept-frequency lasers," European Quantum Eletronics Conference, 2005 *EQEC '05) Jun. 12-17, 2005, p. 204.
ISR for PCT/CA2007/002306 dated Apr. 17, 2008.
Office action for CA2671122 dated Jun. 13, 2011.
Harren et al., Photoacoustic Spectroscopy in Trace Gas Monitoring, encyclopedia of Analytical Chemistry, pp. 2203-2226, J. Wiley and Sons, 2000.
Freed, C., Status of CO2 Isotope Lasers and Their Applications in Tumable Laser Spectroscopy, IEEE Journal of Quantum Electronics, vol. QE-18, No. 8, 1982.
Sharpe et al., "Gas Phase Databases for Quantitative Infrared Spectroscopy," Applied Spectroscopy, vol. 58, No. 12, 2004.
Akaike, H., "A new look at the statistical model identification," IEEE Transactions on Automatic Control, 19(6): 716-723, 1974.
Cormier, John G., "Development of an Infrared Cavity Ringdown Spectroscopy Experiment and Measurements of Water Vapor Continuum Absorption.," Thesis, 2002.
Kurochkin et al., "Three Mirror Cavity CO2 Lser for Inactivity Saturated-Absorption Spectroscopy." Optical Spectroscopy, vol. 65, No. 2, pp. 265-267, Aug. 1988.
Office Action for U.S. Appl. No. 12/517,036 dated Dec. 14, 2011.
Fuchs, D., et al., "Decline of exhaled isoprene in lung cancer patients correlates with immune activation," Journal of breath research 6.2 (2012): 027101+B8.
Ligor, Magdalena, et al., "Determination of volatile organic compounds of exhaled breath of patients with lung cancer using solid phase microextraction and gas chromatography mass spectrometry," Clinical chemistry and laboratory medicine 47.5 (2009): 550-560.
Vaughan, Christina, et al., "Automated determination of seven phenolic compounds in mainstream tobacco smoke," Nicotine and Tobacco Research 10.7 (2008): 1261-1268.
Cope, et al., "Effects of ventilation on the collection of exhaled breath in humans," J. App I Physiol 96: 1371-1379: 2004.
Office action for U.S. Appl. No. 14/720,447 dated Apr. 6, 2017.
Office action for U.S. Appl. No. 14/720,447 dated Apr. 19, 2018.
Final office action for U.S. Appl. No. 14/720,447 dated Sep. 13, 2017.
English translation of DE102013215640A1.
Office action for U.S. Appl. No. 14/720,456 dated Jun. 14, 2017.
Office action for U.S. Appl. No. 15/920,212 dated Jun. 27, 2019.
Final Office action for U.S. Appl. No. 15/920,212 dated Oct. 3, 2019.
Notice of Allowance for U.S. Appl. No. 15/920,212 dated Jan. 23, 2020.
International Search Report and Written Opinion for PCT/CA2020/050252 dated May 12, 2020.
International Search Report and Written Opinion for PCT/CA2020/050250 dated May 22, 2020.
International Search Report and Written Opinion for PCT/CA2020/050/249 dated Apr. 29, 2020.
International Search Report and Written Opinion for PCT/CA2020/050248 dated Jun. 11, 2020.

* cited by examiner

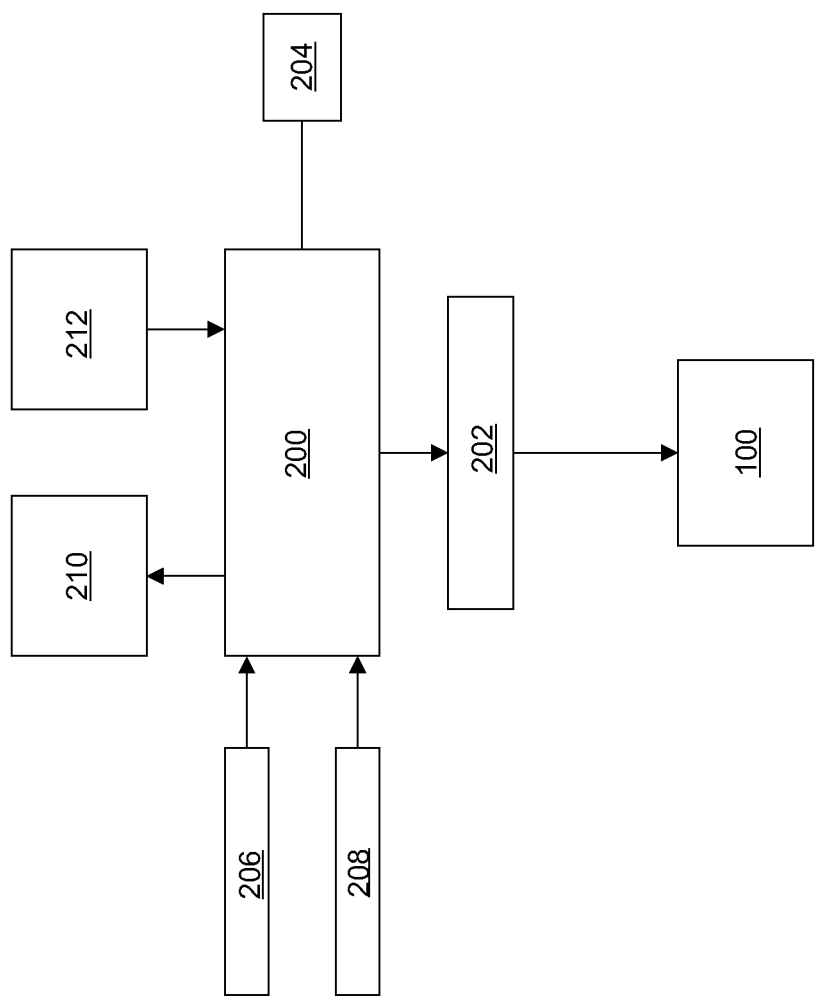

ALVEOLAR BREATH COLLECTION APPARATUS

PRIORITY APPLICATIONS

This application is a continuation-in-part application of U.S. application Ser. No. 14/720,456 filed on May 22, 2015, which claims the benefit of U.S. Provisional Application No. 62/002,159 filed on May 22, 2014, the content of each being incorporated herein by reference in its entirety.

TECHNICAL FIELD

An improved apparatus for medical diagnostics is provided. More specifically, an improved apparatus for receiving and sampling volatile organic compounds (VOCs) from at least one gas sample is provided, some or all of the gas sample comprising human alveolar breath.

BACKGROUND

The analysis of volatile organic compounds (VOCs) in exhaled human breath is rapidly emerging as a painless, non-invasive alternative to conventional methods of disease diagnosis and metabolite measurement. Breath VOC measurement is also commonly used for monitoring the effects of human exposure to environmental pollutants and drugs.

Hundreds of VOCs have been found in exhaled human breath, many of which originate from blood-air exchange in the lower (i.e. alveolar) area of the lungs. Because these compounds are mostly present at very small concentrations (parts-per-billion or less), their measurement by instruments such as GC-MS (Gas Chromatography-Mass Spectrometer) or infrared cavity-enhanced technologies often requires pre-concentration by filtering out undesired compounds such as nitrogen ($N_2$) and oxygen ($O_2$). The relatively large quantities of water vapour and carbon dioxide ($CO_2$) present in exhaled breath should also be filtered out since they can hinder measurement of remaining VOCs in instruments such as GC-MS and IR spectrometers.

U.S. Pat. No. 5,465,728 to Philips discloses an apparatus which is used to collect mammalian breath for chemical analysis and as a diagnostic tool for the physician. The apparatus comprises a fluid reservoir container having first and second ends and a body extending between these ends so as to define an interior chamber; a breath entry portal; a breath exit portal; a sampling portal; a jacket to maintain the temperature of the chamber; a sample container for holding samples of exhaled breath; and pump means for moving selected samples of breath from the reservoir container into the sample container.

U.S. Pat. No. 6,726,637 also to Philips discloses an arrangement for the collection, concentration, and optional analysis of volatile organic components in alveolar breath that includes a condensation unit which removes water vapor from the alveolar breath. The arrangement has two significant shortcomings. The first is that the disclosed method for alveolar sampling is based on assumptions of the subject's lung capacity and expiration rate. The method is therefore subject to inaccuracies in cases where a particular subject's lung capacity and/or expiration rate deviates strongly from the normal assumptions. Furthermore, there is no discussion about how cross-contamination of VOCs between subjects is prevented or otherwise dealt with.

U.S. Pat. No. 6,582,376 to Baghdassarian discloses a device for collecting alveolar breath. Breath is expired into the inlet of a hollow body. The hollow body has two outlets, with a valve disposed in each outlet. The concentration of a specific gaseous component of expired breath is monitored by a gas concentration monitor as the expired breath passes through the hollow body to determine when alveolar breath is present in the hollow body. When alveolar breath is present in the hollow body, the valve in the second outlet is actuated to an open position to collect the alveolar breath in the collection reservoir affixed to the hollow body at the second outlet. While the Baghdassarian apparatus employs a $CO_2$-based method for discriminating between alveolar and tidal breath, it is unable to concentrate VOCs and is unable to remove undesired $CO_2$ and water from the breath sample.

United States Patent Application Publication No. 2004/0162500 to Kline discloses a diagnosis method for respiratory disease based on the separation of the expired airway phase in an exhaled breath from the alveolar phase, and a device to accomplish the method. The device includes a cartridge assembly and a disposable condensing chamber carried in a substantially enclosed housing. The cartridge assembly includes a disposable cartridge and a reusable control system that monitors a characteristic of gas passing through the cartridge to determine when to divert the exhaled breath to an exhaust outlet and when to divert the exhaled breath to the condensing chamber. The characteristic is selected as being representative of the transition from the expired airway phase to the alveolar phase. Also included are a refrigeration system, an auxiliary monitoring system for determining when a sufficient volume of gas has been produced, and a built-in analyzer.

The Kline device contains a mechanism capable of diverting the non-alveolar component of breath from being collected and concentrated, based on the measurement of some characteristic of the exhaled breath passing through. However, the Kline Apparatus is designed to collect breath water vapour for subsequent analysis of the breath condensates found therein, and is not appropriate for applications where it is desirable to filter out such water and to concentrate remaining breath VOCs.

United States Patent Application Publication No. US 2015/0335267 to Cormier discloses an apparatus for collecting breath VOCs having sorbent tubes to filter out nitrogen, oxygen, water, and carbon dioxide, a capnometer or other device for discriminating between alveolar and non-alveolar portions of exhaled breath, a flowmeter for measuring volume of exhaled breath, and a collection chamber, such as a piston, for collecting and concentrating exhaled breath. Cormier discloses the use of a pump to draw captured breath from the collection chamber through one or more of the sorbent tubes. While the apparatus taught in Cormier is capable of isolating and concentrating the alveolar portion of exhaled breath, the use of a pump to deliver collected breath to the sorbent tubes can be problematic, as using a pump to draw collected breath from the collection chamber lacks responsiveness and precision, and can also be unsafe to the user. The lack of precision results from an "all-or-nothing" approach where the collection chamber must be completely filled and completely emptied, with no opportunity to fill only a portion of the collection chamber, or draw a portion of the collected breath as there is no method of determining how much breath has been collected in, or drawn from, the collection chamber. Further, as not all of the alveolar breath flowing to the collection chamber is collected, and some flows out through the exhaust port connected to the piston, the device in Cormier must over-sample breath in order to collect the requisite volume of alveolar breath. Additionally, as the capnometer and flowmeter in Cormier are positioned in-line with the collection chamber, there is a risk of accumulated particles in the capnometer/flowmeter from prior samples contaminating new breath samples. The system in Cormier is also unable to pump room air through the capnometer and flowmeter during sampling procedures to remove condensation from the components and the line, which is desirable as condensation can accumulate contaminants. Similarly, arranging the flowmeter and capnometer in-line with the rest of the system results in a longer travel distance between the mouthpiece and the collection chamber, which provides more opportunities for contaminants to collect. Further, the Cormier system, which is restricted to the use of a 4-way valve design, only permits one flow path to be open at a time, precluding the possibility of cleaning or flushing procedures with room air. There is a need for an improved, more accurate apparatus for collecting and sampling volatile organic compounds from some or all of the collected gas sample.

SUMMARY OF THE INVENTION

According to embodiments herein, an apparatus for collecting a gas sample and sampling volatile organic compounds from the collected gas sample is provided, the apparatus for the improved collection and storage of volatile organic compounds (VOCs) from a gas sample for future analysis, the gas sample comprising, for example, human breath or/or ambient air. More specifically, the apparatus is configured to receive a gas sample, via a gas inlet, into an exhaust portion via a gas exhaust line, into a gas collection and sampling portion via a gas collection line, or both simultaneously. The exhaust portion and the gas collection and sampling portions may be in fluid communication with the gas inlet and with one another. In some embodiments, the apparatus may further comprise at least one auxiliary gas inlet port.

In some embodiments, the exhaust portion may be configured to provide a gas volume measuring device, positioned on the exhaust line, for measuring the volume of the gas sample. The exhaust portion may further be configured to provide a gas monitoring device, positioned on the exhaust line, for measuring and monitoring at least one physical characteristic of the gas sample. The gas volume measuring device may comprise a flowmeter, and the gas monitoring device may comprise a capnometer.

The exhaust portion may further comprise at least a first gas outlet for venting some or all of the gas sample from the apparatus. The exhaust portion may further comprise at least a second gas outlet for venting ambient air passing through the exhaust line out of the apparatus (i.e. flushing the exhaust line). In some embodiments, the exhaust portion may comprise a pump for controllably passing the ambient air along the exhaust line, flushing the exhaust line.

In some embodiments, the gas collection and sampling portion may be configured to provide a first gas collection portion, positioned on a first branch of the gas collection line, the gas collection portion forming a gas collection chamber for receiving the portion of the gas sample, and a second gas sampling portion, positioned on a second branch of the gas collection line, the gas sampling portion formed to provide at least one gas sampling device for sampling volatile organic compounds from the gas sample. In other embodiments, the gas collection and sampling portion may further be configured to provide an ambient air component, positioned on a third branch of the gas collection line, for collecting and sampling ambient air from the environment. In some embodiments, the gas sampling devices may comprise thermal desorption tubes designed to filter out undesired compounds such as, without limitation, nitrogen, oxygen, water, and/or carbon dioxide.

In some embodiments, the first gas collection portion may be configured to provide a gas collection chamber for receiving a portion of the gas sample. The chamber may be formed to receive a reciprocating piston therein. The piston may be operably connected to a drive mechanism for actuating the piston between a first compressed position and a second decompressed position, such actuation drawing at least a portion of the gas sample into the collection chamber or, in reverse, to expel at least a portion of the gas sample collected and stored within the chamber.

In other embodiments, a method for collecting a gas sample and sampling volatile organic compounds from the collected gas sample is provided, the method comprising receiving the gas sample within a gas collection and sampling apparatus, measuring the flow of the gas sample, and monitoring and detecting at least one physical characteristic of the gas sample, and venting at least one first portion of the gas sample until a threshold flow rate and threshold level of the at least one physical characteristic is detected, directing at least one second portion of the gas sample to at least one gas sampling device for sampling at least one volatile organic compound from the sample.

In some embodiments, the flow of the gas sample is measured by a gas volume measuring device, such as a flowmeter, and the at least one physical characteristic is monitored and detected by a gas monitoring device, such as a capnometer. The at least one physical characteristic may comprise the level of carbon dioxide in the sample.

In some embodiments, the apparatus may further comprises a gas collection chamber having a reciprocating piston slidably received therein and the directing of the at least one second portion of the gas sample comprises controllably actuating the piston from a first compressed position to a second decompressed position. In other embodiments, the apparatus further comprise a gas collection chamber for receiving and collecting at least a portion of the gas sample, and at least a portion of the venting of the at least one first portion of the gas sample and the collection of at least a second portion of the gas sample may occur simultaneously. The gas sample may comprise a sample of human breath or ambient air. Where the sample is human breath, the sample may further comprise alveolar air.

BRIEF DESCRIPTION OF THE DRAWINGS

Embodiments of the invention will now be described with reference to the appended drawings in which:

FIG. 5 is a block diagram of components of the breath collection apparatus of FIG. 1, in communication with a microprocessor.

DETAILED DESCRIPTION

According to embodiments herein, an apparatus 100 is disclosed for the improved collection and storage of volatile organic compounds (VOCs) from a gas sample for future analysis, the gas sample comprising, for example, human breath or/and ambient air. As would be understood, the collected and stored VOCs may be subjected to further analysis via, for example, the Laser Infrared Sample Analysis (LISA) device disclosed in U.S. Pat. No. 8,288,727, to Cormier et al., the contents of which are incorporated herein by reference in their entirety.

Figure 1:
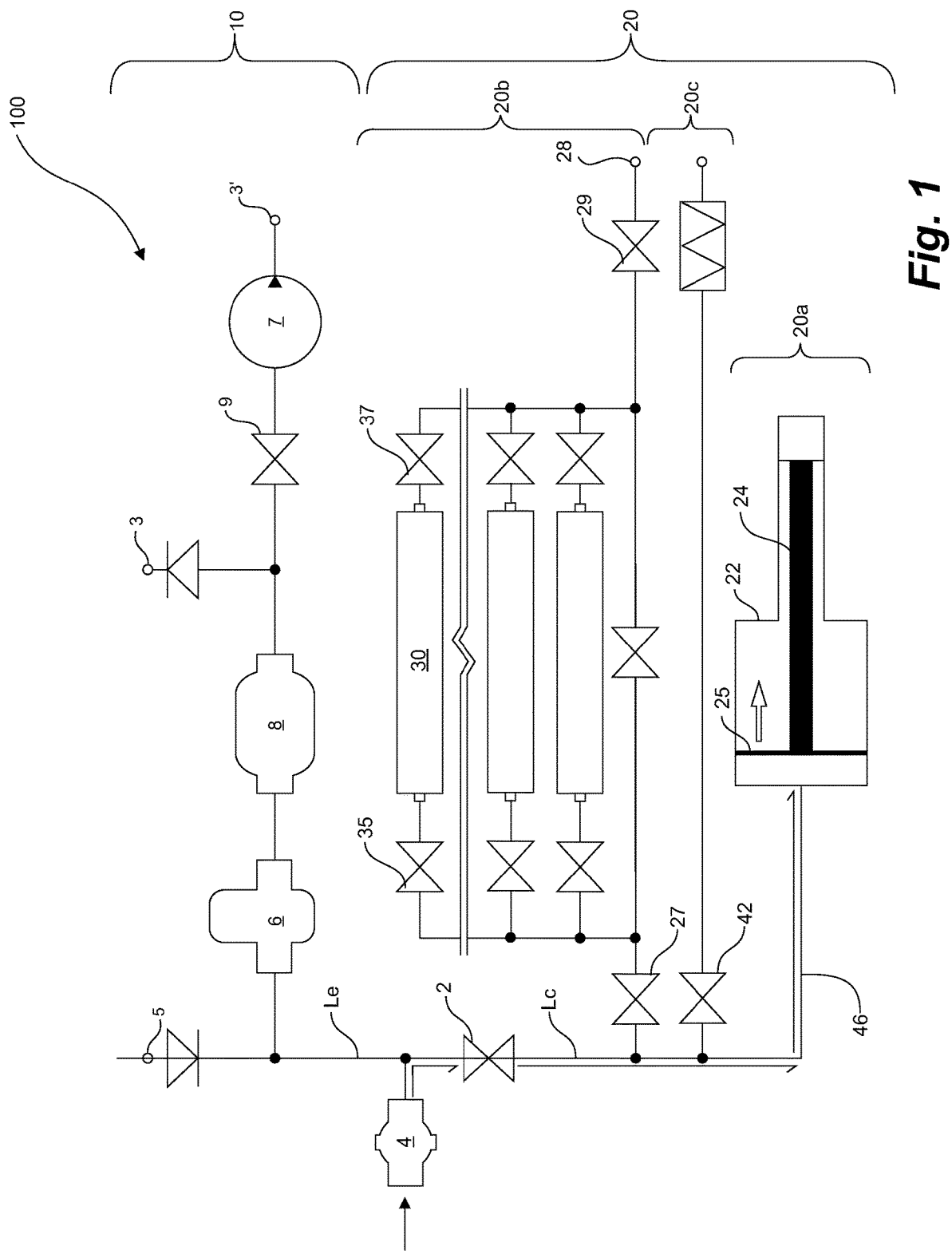
FIG. 1 is a schematic diagram of the present apparatus according to embodiments herein, the apparatus comprising an exhaust portion and a collection and sampling portion.

FIG. 1 provides a schematic diagram of components of the improved gas sampling apparatus 100, according to embodiments herein. Generally, apparatus 100 may comprise at least an exhaust portion 10 and a gas collection and sampling portion 20. As will be described in greater detail, apparatus 100 may be configured to receive and collect a gas sample into the collection and sampling portion 20, wherein the gas is collected within a first gas collection portion 20a and delivered to a second gas sampling portion 20b. Herein, the gas collection and sampling portion may be referred to collectively as the "gas collection" portion. Apparatus 100 may further comprise at least one ambient air component 20c, for receiving and sampling ambient air from the environment surrounding the apparatus 100.

Advantageously, apparatus 100 may be configured to provide an improved gas collection mechanism, said mechanism provided more accurate and precise intake of some or all of the gas sample (described in detail below). For example, apparatus 100 may be configured such that components of the apparatus 100 are arranged in a manner to enhance safety and that minimizes cross-contamination of samples within the apparatus 100, and in a manner that allows for fast and efficient flushing (i.e. clearing or cleaning) of lines within the apparatus 100. Apparatus 100 will now be described in greater detail having regard to FIGS. 1-5.

Herein, reference to general terms such as "upstream" and "downstream" are relative terms used for explanatory purposes only. Gas samples referred to herein may mean, for example, a human breath sample, an ambient air sample, or a combination thereof. Where the gas sample may comprise a human gas sample, the gas sample may contain alveolar air within the sample.

Having regard to FIG. 1, apparatus 100 may comprise a first exhaust portion 10 housed within apparatus 100 and operatively connected in parallel and in fluid communication to the second gas collection and sampling portion 20. Exhaust portion 10 may be connected to the collection portion 20 via any means known in the art such as, for example, a two-way valve 2. Two-way valve 2 may serve to reversibly isolate or connect the exhaust and collection portions 10,20. Apparatus 100 may include a gas inlet 4 (e.g. gas intake component, or mouthpiece), fluidly connected to both exhaust and collection portions 10,20. Where the gas sample comprises a sample of human breath, gas inlet 4 may comprise any mouthpiece known in the art into which the subject exhales. Gas inlet 4 may be fitted with a disposable microbial filter (not shown) to prevent infection and transfer of bacteria. As will be described in detail below, apparatus 100 may be configured to concentrate a plurality of received gas samples until, for example, a sufficient sample is achieved for sampling. For example, where the gas sample comprises human breath, multiple breath exhalations may be received via gas inlet 4 if desired or needed for testing, the resulting gas sample being a concentrated combination of the multiple breath exhalations.

Figure 2A:
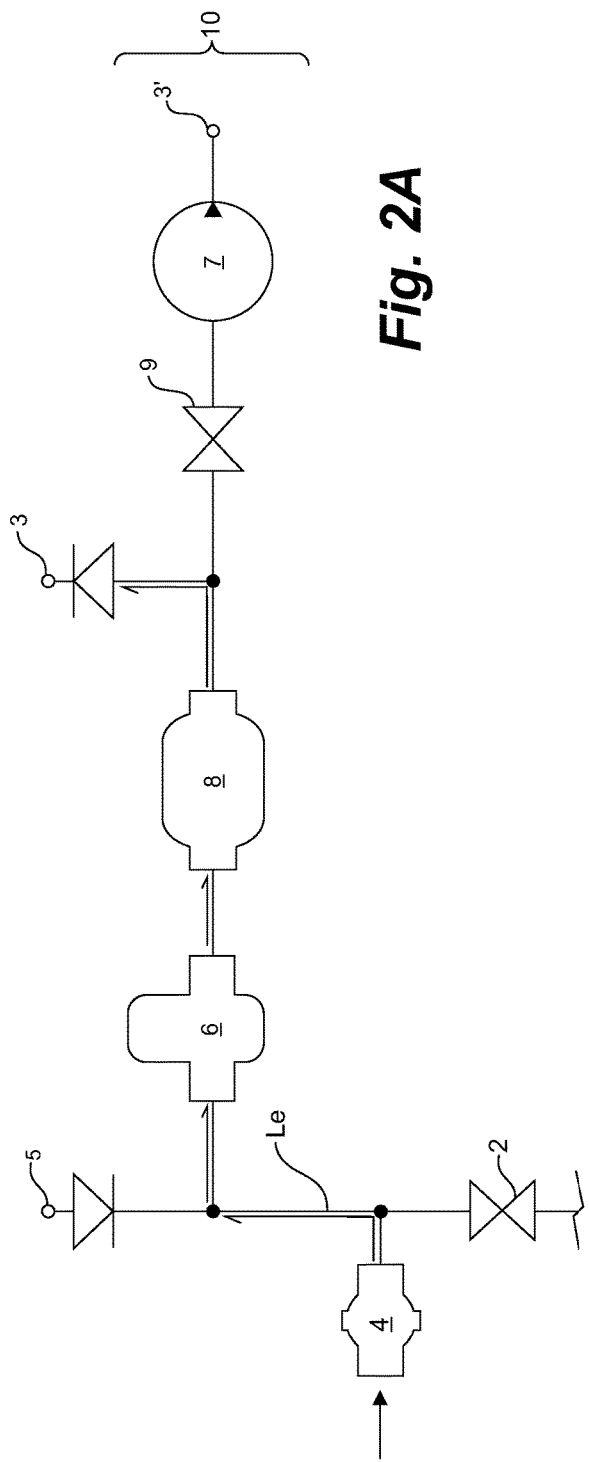
FIG. 2A is a schematic diagram of the exhaust portion of the apparatus of FIG. 1, the exhaust portion configured to vent some or all of an undesired gas sample from the apparatus via first gas outlet.
Figure 2B:
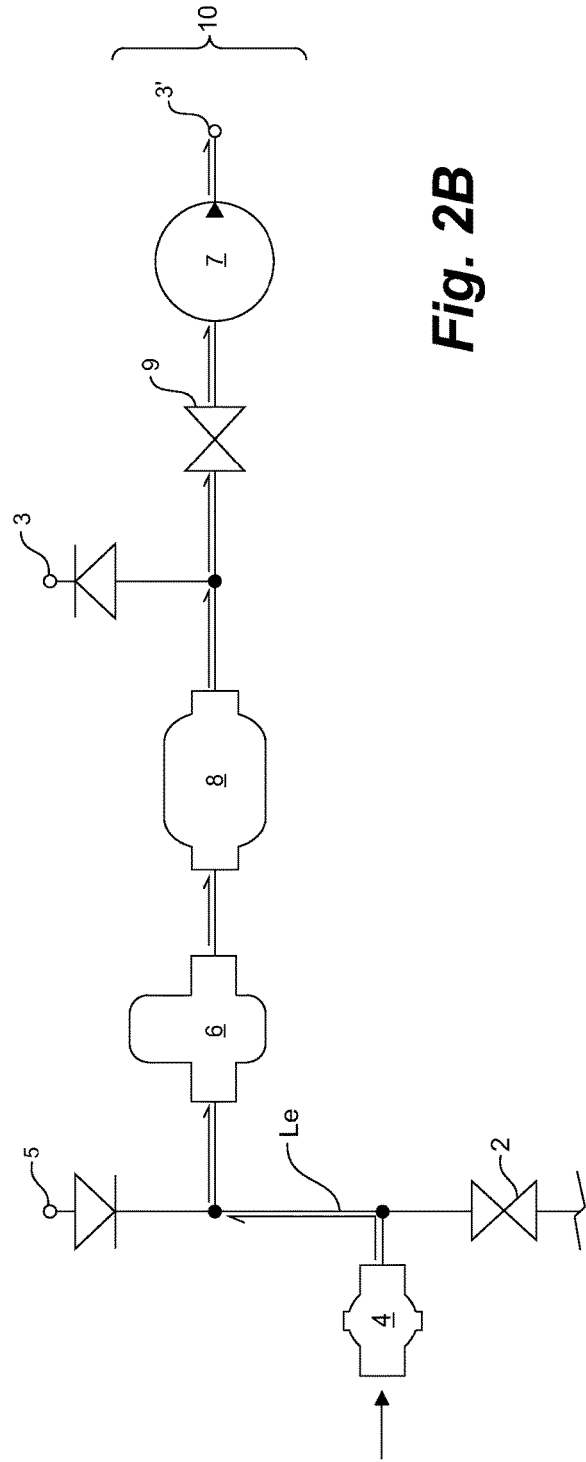
FIG. 2B is a schematic diagram of the exhaust portion of FIG. 2A, the exhaust portion configured to flush a gas sample through the exhaust portion and out a second gas outlet, such flushing operably controlled via at least one pump.

Having regard to FIGS. 2A and 2B, exhaust portion 10 may be configured to measure the volume and the quality of the gas sample received from the gas inlet 4 and, where applicable, to vent some or all of the gas sample. Exhaust portion 10 may be fitted, along an exhaust line $L_e$, with at least one gas volume measurement device 6, such as a flowmeter, for measuring the volume of the gas sample being provided (e.g. a breath sample provided by a subject during exhalation in the gas inlet or mouthpiece). Exhaust portion 10 may be further configured to measure and monitor at least one physical characteristic of the gas sample received from the gas inlet 4. Exhaust portion 10 may be fitted, along the exhaust line $L_e$, with a gas monitoring device 8, such as a capnometer, in fluid communication with gas inlet 4 for receiving the gas sample and discriminating between alveolar and non-alveolar air within the gas sample. In some embodiments, gas monitoring device 8 may determine the concentration of $CO2$ in the gas sample as a means for distinguishing between alveolar and non-alveolar air in the sample, such determination being made in real-time. The $CO_2$-based technique of discriminating between alveolar and non-alveolar breath described above has been shown to be accurate and to allow for a robust normalization of breath VOCs. More information about the $CO_2$-based method may be found in Cope et al., *Effects of ventilation on the collection of exhaled breath in humans*, J App l Physiol 96: 1371-1379, 2004.

Where the gas sample is detected as containing undesired gas (e.g. non-alveolar air), apparatus 100 may advantageously be configured to direct some or all of the undesired gas sample out of the exhaust portion 10, thereby expelling the sample from the apparatus 100 (FIG. 2A,2B). Alternatively, where the gas sample is detected as containing desired gas (e.g. alveolar air), apparatus 100 may also be advantageously operative to direct some or all of the desired gas sample, via two-way valve 2, into the gas collection and sampling portion 20 (FIG. 1). In other words, the present exhaust line $L_e$ of the exhaust portion enables the "side-sampling" of the collected gas sample in order to ensure that the sample contains the desired gas prior to the collection thereof (into the gas collection portion).

More specifically, having regard to FIG. 2A, exhaust portion 10 may comprise at least one first gas outlet 3 for expelling gas from the apparatus 100. For example, in some embodiments, gas monitoring device 8 may be operatively in fluid communication with gas volume device 6, such that, in combination, the gas monitoring and volume devices may serve to detect and monitor the flow of the gas sample and, where determined, to operatively vent at least a portion of the gas sample from the apparatus 100. Accordingly, in some circumstances, at least a portion of the gas sample received at the gas inlet 4 may be expelled from the apparatus 100 via at least one first gas outlet 3. It should be understood that the at least one first gas outlet 3 may vent a portion of the gas sample from the apparatus 100 without permitting an influx of ambient from flowing back into the system (e.g. where a subject may inadvertently inhale while engaged with the mouthpiece 4). Moreover, the at least one first gas outlet 3 may be configured in a manner to prevent air from upstream within the exhaust portion 10 from interfering with the measurements of the gas monitoring device 8.

Having regard to FIG. 2B, exhaust portion 10 may be configured in a manner to remove condensation from the exhaust portion 10 (i.e. from the exhaust line $L_e$). For example, in some embodiments, the exhaust portion 10 may further comprise at least one pump 7, located adjacent at least one second gas outlet 3' and downstream at least one valve 9. Where desired, pump 7 may be activated to draw gas (e.g. ambient room air) into the gas inlet 4, through gas volume and gas monitoring devices 6,8, such gas to flush through the exhaust line and exhausted out exhausted out secondary gas outlet 3'. In this manner, the activation of pump 7 may serve to clear the exhaust portion 10 devices and fluid lines communicating there between, preventing the accumulation of condensation and contaminants in devices and the lines.

In other embodiments, optionally and as a safety measure, the exhaust portion 10 of apparatus 100 may further include at least one auxiliary gas inlet port 5 in fluid communication with the exhaust portion 10. Preferably, the at least one auxiliary gas inlet port 5 is positioned in a manner to allow an inflow of ambient air into the apparatus 100 (e.g. when a subject inadvertently seals their mouth to the gas inlet 4 when the apparatus is operating, causing the apparatus 100 to create a negative pressure). Having regard to FIGS. 1, 2A and 2B, the at least one auxiliary gas inlet port 5 may be positioned upstream of devices 6,8, the inlet port 5 having a one-way valve operative to provide a flow restriction path for ambient air to enter the apparatus 100, mitigating or eliminating any potential negative pressure in the system, and alleviating any potential for injury to a subject.

According to further embodiments herein, apparatus 100 may further comprise gas collection and sampling portion 20 (referred to as the "collection portion"), the collection portion 20 configured to both collect the at least one gas sample (e.g. to actively draw in, store, and force out gas samples towards the sampling devices) and to extract or sample VOCs therefrom (e.g. utilizing absorbent or adsorbent materials). Collection portion 20 may be housed within apparatus 100 and operatively connected in parallel and in fluid communication to the exhaust portion 10. It should be understood that the present apparatus 100 is advantageously configured to enable two-flow paths (i.e. the exhaust line and the collection line), such flow paths operative to, where desired, be simultaneously opened and receiving at least a portion of the at least one gas sample. By way of example, during the receiving of the gas sample into the apparatus 100, a portion of the sample (e.g. ~20%) may be directed to the exhaust line for detection and analysis of alveolar vs. non-alveolar breath, while at least another portion of the same sample (e.g. ~80%) may be direct to the collection line for collection (assuming that the portion of the sample being analyzed contains a desired threshold amount of alveolar breath and collection is warranted, see Arrows depicting gas flow in FIG. 3A). Collection portion 20 may be connected to exhaust portion 10 via any means known in the art such as, for example, two-way valve 2. In some embodiments, collection portion 20 may be fitted, along a gas collection line $L_c$, with a plurality of distinct, yet operably coupled components, namely a collection component 20a, a sampling component 20b, and an ambient air component 20c, each described in more detail below. In this regard, gas collection line $L_c$, may be divided, having a plurality of distinct gas lines branching therefrom, and optionally having at least three distinct gas lines (as described below).

Having regard to FIGS. 1 and 3A-3C, at least a portion of the gas samples received via gas inlet 4 may be controllably drawn into and stored into collection component 20a, via a first branch of the gas collection line $L_c$, and directed into at least one collection chamber 22. Gas collection chamber 22 may be in fluid communication with gas inlet 4, for receiving at least a portion of the gas sample directly therefrom. Gas samples may be continually drawn into and stored within collection chamber 22 until a sufficient volume and quality of sample is achieved (i.e. for sampling and/or analysis).

Figure 3A:
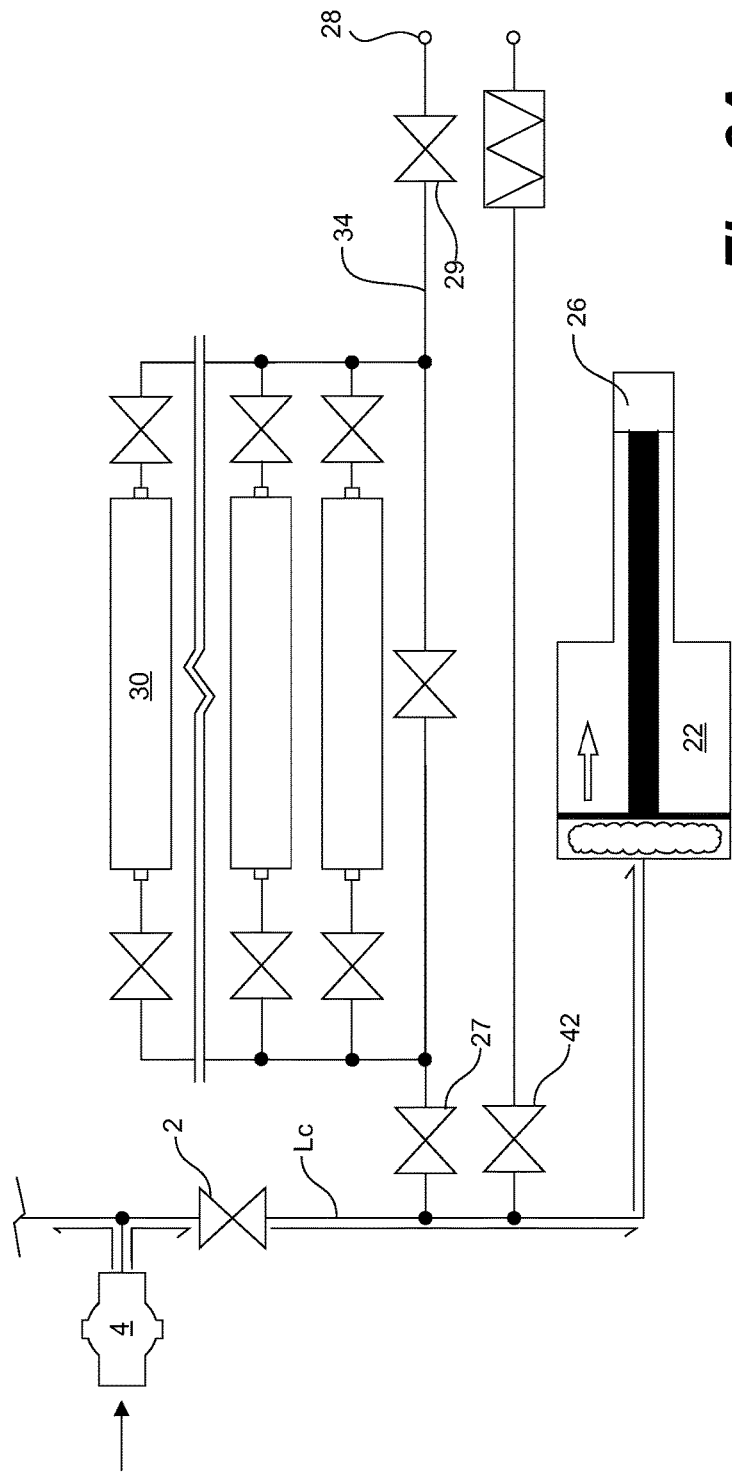
FIG. 3A is a schematic diagram of the collection and sampling portion of the breath collection apparatus of FIG. 1, the collection and sampling portion comprising a collection component, and wherein at least a portion of the gas sample entering the apparatus is shown being directed towards a collection chamber within the collection component (the chamber being "closed")
Figure 3B:
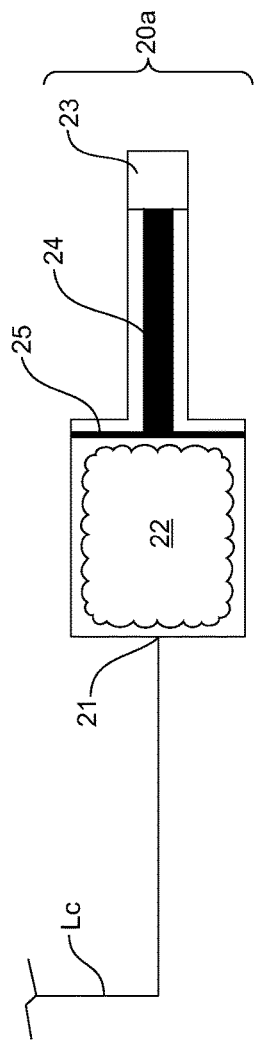
FIG. 3B is a schematic diagram showing the collection component of the collection and sampling portion of FIG. 3A in isolation (the chamber being "open")

Having specific regard to FIG. 3B, in some embodiments, gas collection chamber 22 may comprise a generally tubular housing having a first end 21 and a second end 23. At least a portion of the gas samples entering collection portion 20a may be received within gas collection chamber 22, via a first branch of the gas collection line $L_c$, and stored therein. In some embodiments, at least a portion of the gas samples received via inlet 4 may be directed, via two-way valve 2, along gas collection line $L_c$, into chamber 22, such process continuing until a sufficient volume of sample is received within chamber 22. It should be understood that the sufficient volume of gas sample received and stored within collection chamber 22 may depend upon the particular gas sample being collected and upon the particular VOCs being collected therefrom (e.g. the volume of ambient air and/or alveolar breath required to be collected for certain VOCs to be tested). By way of example, where the apparatus 100 is arranged to sample VOC type "A", collection of at least a portion of a gas sample may require 20 L of collected gas sample to obtained, whereas where the apparatus 100 is arranged to sample VOC type "B", collection of at least a portion of a gas sample may only require 10 L of collected gas sample to be obtained.

Chamber 22 may form an inner diameter configured to receive at least one reciprocating piston 24 therein. Piston 24 may be configured to have a first piston head portion 25 (i.e. piston head portion 25 may extend across the entire cross-section of chamber 22), and a second piston shaft portion, the piston slidably actuable within collection chamber 22. In some embodiments, piston 24 may be controllably coupled to a drive mechanism 26, the drive mechanism 26 operable to actuate piston 24 between a first compressed position and a second decompressed position, wherein in the first compressed positioned (i.e. where the piston 24 is extended away from the drive mechanism and the chamber 22 is "closed"), the piston 26 may be positioned in a manner that little to no gas sample may enter collection chamber 22

Figure 3C:
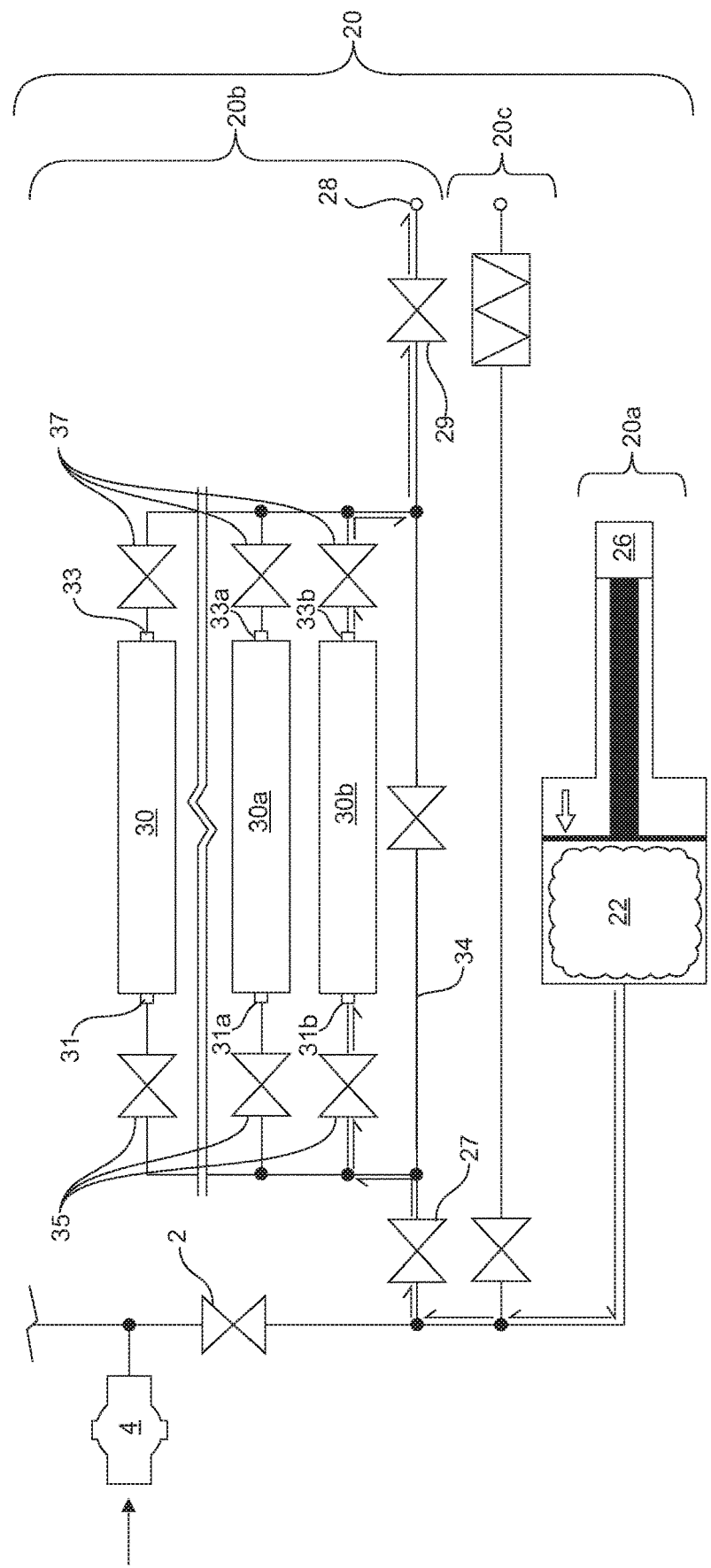
FIG. 3C is a schematic diagram of the collection and sampling portion of the breath collection apparatus of FIG. 1, the collection and sampling portion comprising a sampling component, and wherein at least a portion of the gas sample collected and stored within the collection component is being directed from the collection chamber within the collection component to the sampling component.

(FIG. 3A). In the second decompressed position (i.e. where the piston 24 is retracted and the chamber 22 is "opened"), the piston may be positioned in a manner to draw gas samples into collection chamber 22 (FIG. 3C). In some embodiments, drive mechanism 26 may comprise a motor, such as a stepper motor, or any other such motor operative to actuate piston 44 with increased accuracy.

Advantageously, drive mechanism 26 may serve to accurately actuate piston 24 from the first extended position to the second retracted position as a means of controllably drawing some or all of a gas sample into chamber 22. Moreover, where chamber 22 contains a sufficient volume of a gas sample, drive mechanism 26 may serve to actuate the piston 24 in reverse (reducing the volume of gas sample within chamber 22 and creating an increase in pressure therein), effectively forcing the volume of gas sample within the chamber 22 out of the chamber 22 and towards the sampling component 20b. Piston 24 may be operably connected to drive mechanism 26 at its second shaft end. Arrows in FIGS. 3A and 3C denote translation of piston 24 between the compressed and decompressed positions, while gas cloud schematic denotes at least a portion of the gas sample within chamber 22, increasing or decreasing with the compression/decompression of the piston 24. While reference shall be made herein to a "piston", it would be understood that any other suitable devices operable to compress gas samples may be used in place of the piston without substantially altering the apparatus 100.

As above, gas collection and sampling portion 20 of apparatus 100 may further comprise a sampling component 20b. Having specific regard to FIG. 3C, sampling component 20b may be in fluid communication with collection component 20a, such that sampling component 20b may receive some or all of the gas sample received and stored within collection component 20a. The transmission of some or all of the gas sample into sampling component 20b may be controlled via first sampling valve 27. In some embodiments, sampling valve 27 may be positioned along the gas collection line $L_c$, i.e. along a second branch of the gas collection line $L_c$, in a manner to effectively connect or isolate the sampling component 20b from the other components of apparatus 100. As would be understood, apparatus 100 may further comprise a manifold (not shown), for releasably receiving and securing the at least one sampling devices 30. In operation, when the at least one sampling device 30 is secured to manifold, fluid communication is established between the input and output connections 35,37 of the sampling tubes 30.

Sampling component 20b may be operative to receive and collect some or all of the gas sample within apparatus 100 for further analysis. In some embodiments, sampling component 20b may be configured to perform analytical thermal desorption of some or all of the gas sample. In that regard, sampling component 20b may comprise at least one sampling device 30 (30a, 30b, . . . 30n), such as a thermal desorption tube, or other suitable device, having a sorbent material for sampling the gas sample. Thermal desorption tubes may be operative to collect desired VOCs from the gas sample by diffusion of the VOCs onto the tubes packed with the sorbent, while filtering out any undesired compounds. For example, thermal desorption tubes may be operative to collect VOCs of interest within the sample while filtering out compounds such as such as nitrogen (N2), oxygen (O2), water (H2O), carbon dioxide (CO2), etc. Thermal desorption tubes may comprise, for example, adsorbent materials such as Chromosorb® or Tenax®, which allow small molecules such as water (H2O) and carbon dioxide (CO2) to pass through while adsorbing or collecting the remaining larger VOCs of interest. As would be understood, apparatus 100 may be configured to incorporate different sampling devices 30 having different sorbent materials such that different VOCs can be sampled. As would be understood, the at least one sampling devices 30 may be removed and replaced from apparatus 100. For example, upon sampling, the at least one sampling devices 30 may be removed from apparatus 100 for further gas analysis. By way of example, further analysis may be performed by any suitable device such as the apparatus disclosed in U.S. Pat. No. 8,288,727 to Cormier et al., the contents of which are incorporated herein by reference in their entirety.

Having further regard to FIG. 3C, in some embodiments, sampling component 20b may be positioned on a second branch of the gas collection line $L_c$, with each sampling device 30 having corresponding gas inlet ports 31 (31a, 31b, . . . 31n) and gas outlet ports 33 (33a, 33b, . . . 33n). In some embodiments, some or all of the gas sample may be directed to the at least one sampling devices 30 via corresponding input control valves 35. Some or all of the gas sample may be directed out of the at least one sampling device 30 via output control valves 37. Following sampling, some or all of the gas sample exiting the at least one sampling device 30 may be expelled from apparatus 100 via gas exhaust port 28, such expulsion controlled via at least one exhaust valve 29. As depicted in FIG. 3C, gas exhaust port and valve 28,29 may be positioned along the second branch of the gas collection line, at a terminal end thereof, and downstream of the at least one sampling devices 30.

Having further regard to FIG. 3C, sampling component 20b may further comprise an optional gas bypass line 34, said bypass line 34 also stemming from the second branch of the gas collection line $L_c$. For example, in some embodiments, bypass line 34, may be primed with some or all of the gas sample (e.g. with alveolar or ambient air), or flushed with ambient air to clean all of the gas lines within the sampling component 20b (e.g. when the at least one sampling devices 30 have been removed from the apparatus 100 and the valves 35,37 are open, and bypass valve 39 is open).

Figure 4A:
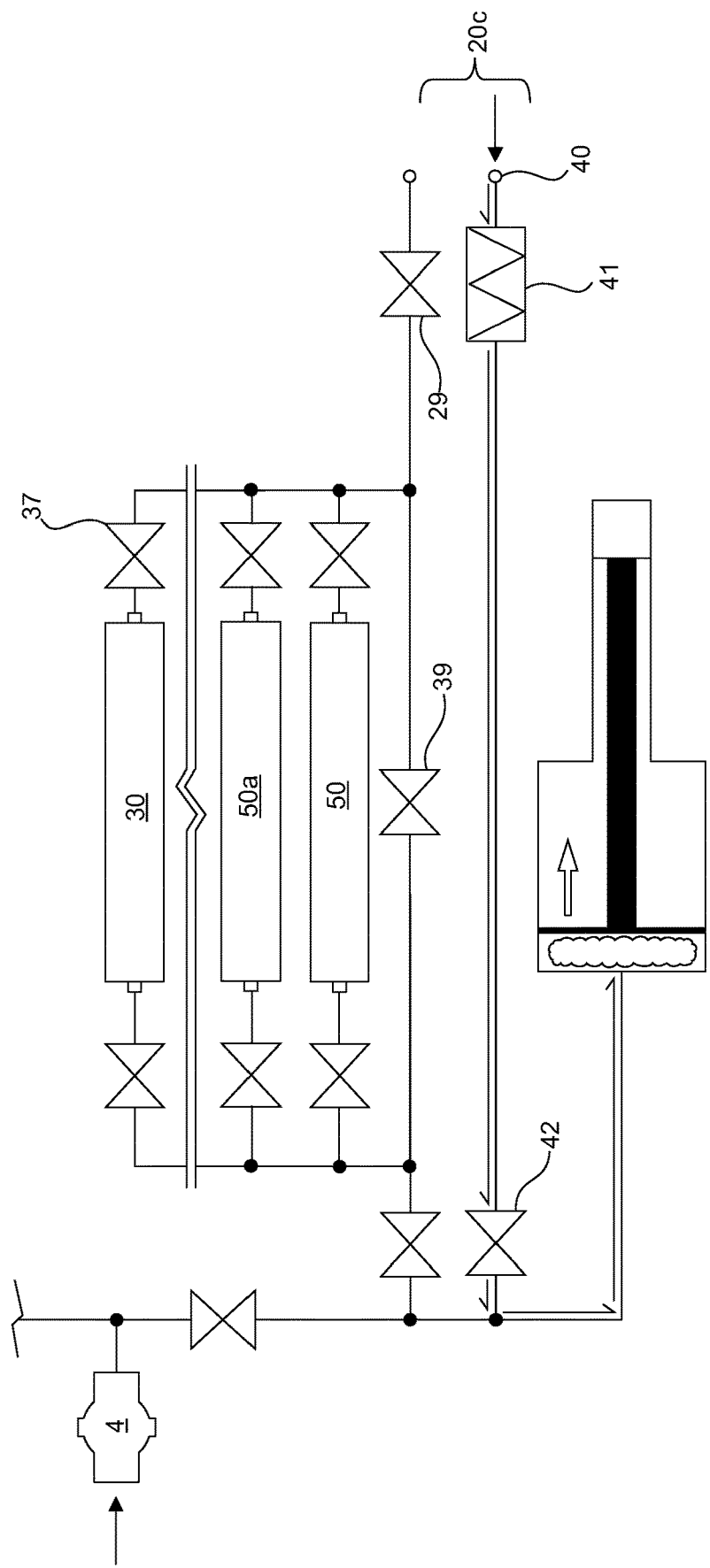
FIG. 4A is a schematic diagram of the collection and sampling portion of the breath collection apparatus of FIG. 1, the collection and sampling portion comprising a purge component providing a flow of ambient air into the apparatus and towards the collection chamber of the collection component.
Figure 4B:
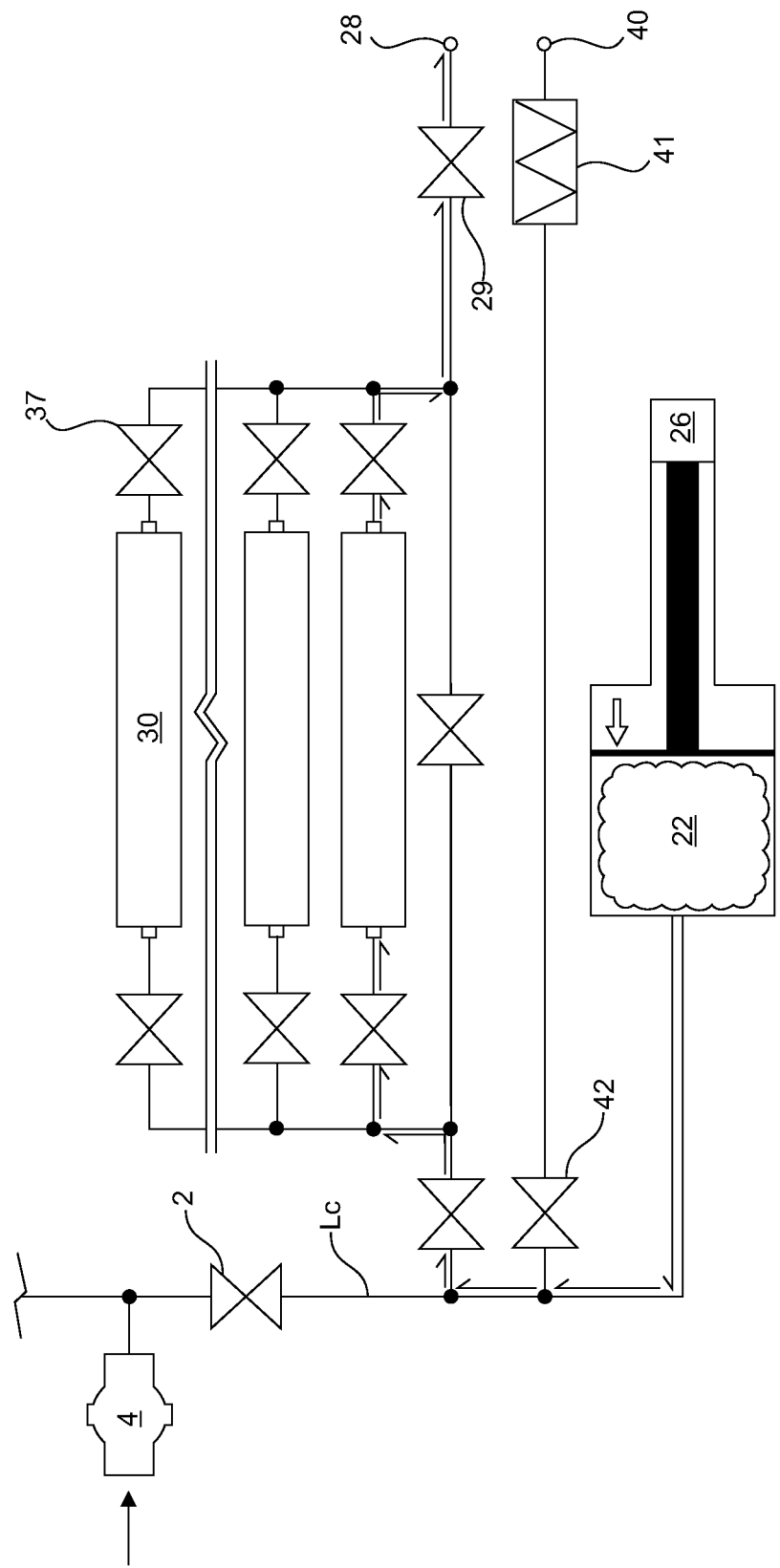
FIG. 4B is a schematic diagram of the collection and sampling portion of the breath collection apparatus of FIG. 1, the collection and sampling portion comprising a purge component providing a flow of ambient air into the apparatus and towards the sampling component.

As above, having regard to FIGS. 4A and 4B, apparatus 100 may further comprise an optional ambient air component (e.g. ambient air intake component) 20c, the ambient air component 20c configured to draw a sample of ambient air from the environment into apparatus 100, via ambient air intake 40. Ambient air component 20c may be housed within apparatus 100 and operatively connected in parallel and in fluid communication to gas collection and sampling components 20a,20b. In some embodiments, ambient air component 20c may comprise a third branch of the gas collection line Lc, whereby some or all of the sample of ambient air received by apparatus 100 may be directed to gas collection component 20a (FIG. 4A) and/or gas sampling component 20b (via the gas collection component 20a; FIG. 4B). In operation, ambient air may be received by the apparatus 100 and collected in chamber 22 of the gas collection component 20a. Once collected, some or all of the ambient air may then be conveyed from the gas collection portion 20a to the gas sampling portion 20b (e.g. for sampling of VOCs therefrom), as described above. Advantageously, in this manner, one or more VOCs contained within the ambient air sample may be compared to the VOCs from one or more of the gas samples provided to apparatus 100, such comparison performed to determine, for example, whether the VOCs measured in the gas sample might be produced endogenously by a subject providing the gas sample, or as a result of the subject having inadvertently inhaling ambient air prior to providing the gas sample.

Having regard to FIG. 4B, in some embodiments, ambient air component 20c may comprise at least one filter 41, such as a dust filter, positioned on the ambient air line, for filtering contaminants and other unwanted particles from the ambient air sample received via intake 40. In some embodiments, at least one ambient air control valve 42 may be positioned along the ambient air line and downstream of the ambient air intake 40, for controllably connecting or isolating ambient air portion 20c from the other components of apparatus 100 (e.g. exhaust and collection components 10,20).

According to embodiments herein, apparatus 100 may be operated manually, automatically, or a combination thereof. Having regard to FIG. 5, at least one microprocessor 200 may be provided, such microprocessor 200 operably connected to, at least, some or all of the actuable components within apparatus 100 (e.g. without limitation, the drive mechanism, flowmeter, capnometer, one- and two-way valves, and/or pump). Microprocessor 200 may activate apparatus 100 via at least one relay array 202.

For example, in some embodiments, the at least one microprocessor 200 may be of executing computer readable program code stored on a computer readable medium 204 Computer readable medium may include a main memory 206, such as a random access memory (RAM) or other dynamic storage device (e.g., dynamic RAM (DRAM), static RAM (SRAM), and synchronous DRAM (SDRAM)), in communication with microprocessor 200 for storing information and instructions to be executed by microprocessor 200. The main memory 206 may be used for storing temporary variables or other intermediate information during the execution of instructions by the microprocessor 200. Microprocessor 200 may include memory structures such as registers for storing such temporary variables or other intermediate information during execution of instructions 208. Apparatus 100 further includes a read only memory (ROM) or other static storage device (e.g., programmable ROM (PROM), erasable PROM (EPROM), and electrically erasable PROM (EEPROM)) in communication with microprocessor 200 via a bus or other communications structure for storing static information and instructions for the microprocessor.

The apparatus 100 can also have a user interface display 210 connected to microprocessor 200 for displaying status information and having a touch-button interface 212 for control by an operator of apparatus 100.

EXAMPLES

By way of the following Example, the present apparatus 100 will now be described in operation.

In preparation for gas sampling procedures, valves along the collection line $L_c$ (e.g. valves 2, 27, 42), valves providing gas samples to and from the at least one sampling devices 30 (e.g. valves 35, 37, 29), are closed, and piston 24 is actuated into the fully compressed or extended position. One or more new at least one sampling devices 30 are placed into the apparatus 100 (i.e. the manifold therein), such that input/output valves 35,37 and corresponding input/output line connections are in fluid communication.

To begin, the operator activates the instruction set stored in the computer readable medium 204 of apparatus 100 via the touch-button interface 212, such that apparatus 100 in turn displays instructions for a subject via user interface display 210. The subject is prompted to draw in a breath and to exhale the breath into the gas inlet 4. As depicted in FIG. 2A, during the first part of the exhalation, which can commonly comprise non-alveolar breath, valve 2 remains closed such that flow of the non-alveolar breath is directed to the exhaust portion 10. As would be understood, the gas sample is directed along the exhaust line $L_e$ to the gas volume measuring device 6 and the gas monitoring device 8. The gas sample may then be vented from apparatus 100 via first gas outlet 3. The subject may then be prompted to provide one or more gas samples into inlet 4 and the foregoing is repeated. As more of the at least one sample passes along the exhaust line $L_e$, gas monitoring device 8 may detect that the CO2 levels in the sample has reached and stabilized at or above an appropriate threshold level to indicate that the sample primarily contains alveolar breath. At this time, microprocessor 200 may be automatically activated to respond by signalling relay array 202 to open valve 2, and to trigger drive mechanism 26 to begin actuating piston 24 towards the decompressed position, opening collection chamber 22, drawing the gas sample received by apparatus 100 into the collection chamber 22. As the piston 24 translates from the extended position to the retracted position, at least a portion of the alveolar breath may still be directed through the exhaust portion 10 along the exhaust line $L_e$. In this regard, gas volume measuring device 6 may continue to measure the volume of gas passing through the device (i.e. the flow rate of the gas sample). The actual (total) exhalation flow rate can be calculated by adding the flow rate measured by the gas volume measuring device 6 with the volumetric rate (e.g. the speed) at which the piston 24 actuates. The volumetric rate at which piston 24 is translated towards the retracted position should be less than the total exhalation flow rate, thereby avoiding the creation of a negative pressure while collecting the gas sample (i.e. the alveolar breath sample). Advantageously, the translation rate of the piston 24 can be precisely controlled, and can further be adjusted periodically to account for changes in the gas sampling intake rate (i.e. the subject's exhalation rate). In other words, the rate of the piston 24 actuation can be regulated such that the gas volume measuring device 6 continues to measure a positive flow rate through the exhaust portion 10. Precise regulation and control of the rate of expansion of piston 24 is enabled by drive mechanism 26, such that where the total exhalation flow rate of the gas sample falls below a certain threshold, indicating, for example, that the subject is running out of breath, the expansion of piston 24 can be slowed or stopped, and valve 2 closed in order to keep the portion of the gas sample collected in chamber 22 within the chamber 22.

Where it is detected that the volume of gas received and collected within chamber 22 is insufficient for sampling and testing, further gas samples may be provided. For example, the subject may be prompted to draw in and exhale a second breath sample into gas inlet 4, as described above. Subsequent gas samples will be monitored by the gas monitoring device to ensure that, for example, non-alveolar portions of the breath sample will again be vented out of the exhaust portion 10 until a predetermined threshold of alveolar breath (or CO2) is detected. Again, once the threshold is achieved, microprocessor 200 will signal relay array 202 to open valve 2, and to operate drive motor 26 to retract piston 24 further within chamber 22 to again being collecting gas sample therein (and adding to the sample previously collected).

Once a sufficient volume of gas sample is collected within chamber 22, the apparatus 10 is prompted to cease receiving gas samples. The microprocessor 200 signals the relay array 202 to close valve 2 and to open intake valves of the sampling component 20b (e.g. valves 27,35,37,29), thereby establishing fluid communication between the gas collection component 20a and the sampling component 20b. Microprocessor 200 then operates drive mechanism 26 to compress piston 24, directing the collected gas sample within chamber 22 of the collection component 20a, along the collection line $L_c$, to the sampling component 20b. The gas sample passes through the at least one sampling devices 30 and out of the apparatus 10 (e.g. via exhaust port 28). It should be understood that the gas sample may be passed through one or more of the at least one sampling devices 30 simultaneously by opening or closing the appropriate control valves 35,37. If any collected gas sample remains within chamber 22, the above steps can be repeated to convey any residual gas to the sampling devices.

Once a sufficient volume of sampled breath has been delivered to the at least one sampling devices 30, or the piston 24 has reached its fully extended position, the VOCs are sampled and stored within the at least one sampling devices 30 and the microprocessor 200 signals the relay array 202 to deactivate the drive mechanism 26 and to close all valves.

At times, it may be desirable to remove condensation that might have accumulated within the components of the apparatus 100. As above, purging of the exhaust line $L_e$, may be performed by closing valve 2 and opening valve 9. Microprocessor may then activate pump 7 to draw ambient air through inlet 4 and through the exhaust portion 10 via exhaust line $L_e$. Purged ambient air may be vented from the exhaust line via the at least one second outlet 3'. It is an object of the present apparatus 100 that gas monitoring and measuring devices may be easily cleaned of condensation and/or other contaminants therein.

At other times, it may be desirable to sample a gas sample primarily comprising ambient air in order to compare the VOCs in the sample with the VOCs in the ambient air (i.e. baseline VOCs present in the ambient air). As above, sampling of ambient air may be performed by closing valves 2,27 and opening valve 42 of the ambient air component 20c. Drive mechanism 26 may then be activated to actuate piston 24 to draw ambient air into the apparatus 100 via inlet 40, and via optional filter 41, and into chamber 22. Once the desired amount of ambient air has been accumulated within chamber 22, valve 42 may be closed, and control valves allowing the passage of air through the at least one sampling devices 30 can be opened (e.g. valves 27,35,37,29). As above, drive mechanism 26 can then be activated to translate the piston within chamber 22 to direct the ambient air within the chamber out through exhaust port 28. It is an object of the present apparatus 100 to provide a method of sampling ambient air from the environment as a means of detecting VOCs in the ambient air, thereby providing a baseline VOC value in order to determine whether the VOCs sampled from the gas sample are a result of the gas sample or as a result of the ambient air (e.g. whether the VOCs may be a result of the subject drawing in and exhausting ambient air).

At yet other times, advantageously, it may be desirable to flush the lines within the apparatus 100 with ambient air. This may be performed by first removing the at least one sampling devices 30 from the manifold, opening the appropriate valves, and operating the drive mechanism 26 to circulate ambient air through the apparatus 100. Such a flushing process may be performed and/or repeated as needed in order to ensure enhanced circulation of ambient air throughout the apparatus 100.

At yet other times, advantageously, it may be desirable to prime the at least one sampling component 20b with alveolar breath prior to sampling. This may be performed by first collecting alveolar breath into chamber 22, as described above, and then closing the input valves to the at least one sampling devices 35, but opening valves 27,39,29, such that all three valves are opened along bypass line 34. Using the drive mechanism 26, the piston 24 may be partially collapsed, and alveolar air may be circulated from chamber 22 through sampling component 20b (via bypass line 34). When sampling VOCs from ambient air, this process can also be used to prime the sampling component 20b with ambient air by drawing in air through ambient air component 20c instead of alveolar breath from the gas inlet 4.

It is contemplated that alternative embodiments of the present apparatus 100 may be provided. For example, without limitation, the present apparatus may further comprise heaters associated with the sampling devices. Alternatively, additional input and output ports may be introduced to allow for desorption of samples contained in sampling devices to be introduced directly from the apparatus 100 to a VOC measurement instrument. It would be understood that sampling devices could then be conditioned by heating and purging and prepared for the next sample collection, without having to remove the sampling devices from the apparatus 100. Heaters could also be used to heat the lines and components of the device 100, reducing condensation therein. For example, heaters may be used to heat the lines within the apparatus 100 to about 40° C. such that moisture in the exhaled breath, which typically has a maximum temperature of 37° C., is not cooled by the components of the device 100 (and minimizing condensation thereof).

According to embodiments herein, the present apparatus advantageously provides the use of a drive mechanism to controllably and precisely actuate a piston (or other compressible device), improving the accuracy of the collection and sampling of gas. A more efficient apparatus is disclosed, as only the required volume of gas that is collected is provided to the sampling devices, thereby, in some cases, allowing only a single breath sample to be delivered to multiple sampling devices, reducing time spent reacquiring breath samples from the subject. Further, the present use of a drive mechanism allows microprocessor to automatically adjust the rate of gas sample collection much more quickly relative to, for example, known gas sampling apparatuses that employ pumps to actuate a piston, allowing for precise adjustments to the collection of breath so as to collect as much alveolar breath as possible without creating negative pressure in the system. Additionally, the present use of a drive mechanism, instead of a pump, allows for gas volume measuring and gas monitoring devices to be positioned along and exhaust line running in parallel to the collection line (i.e. instead of being in-line therewith). Such a configuration advantageously allows for the volume of breath collected to be determined by how much the piston has been expanded by the drive mechanism, thus reducing the risk of cross-contamination between the devices and the collection components. Further still, the present use of the drive mechanism to actuate a piston advantageously allows for collected air or breath in the collection chamber to be directed to multiple parts of the system at once, allowing all the lines of the device to be flushed at once.

Although embodiments have been described with reference to the drawings, those of skill in the art will appreciate that variations and modifications may be made without departing from the spirit, scope and purpose of the invention as defined by the appended claims.

What is claimed is:

1. An apparatus for collecting a gas sample and sampling volatile organic compounds from the collected gas sample, the apparatus comprising:
   a gas inlet for receiving the gas sample;
   a gas collection and sampling portion in fluid communication with the gas inlet via a gas collection line extending from the gas inlet, the gas collection and sampling portion having
      at least a first gas collection portion, positioned on a first branch of the gas collection line, the gas collection portion forming a gas collection chamber for receiving the portion of the gas sample, the chamber formed to receive a reciprocating piston therein, the piston operably connected to a drive mechanism for actuating the piston within the chamber between a first compressed position and a second decompressed position, to draw at least a portion of the gas sample into the chamber, and in reverse between the second decompressed position and the first compressed position, to expel at least a portion of the gas sample stored within the chamber, and
      at least one gas sampling portion, positioned on a second branch of the gas collection line, for receiving the portion of the gas sample expelled from the chamber from the gas collection portion, the gas sampling portion formed to provide at least one gas sampling device configured to capture the volatile organic compounds from the portion of the gas sample received therein; and
   an exhaust portion extending, via an exhaust line, from the gas collection line, the exhaust line having an outlet portion with unidirectional flow away from the gas collection line, the exhaust portion having
      a flowmeter, positioned on the outlet portion of the exhaust line, for measuring the volume of the gas sample, and
      a gas monitoring device fully positioned on the outlet portion of the exhaust line and spaced from the gas collection line, the gas monitoring device being configured to measure and monitor at least one physical characteristic of the gas sample.

2. The apparatus of claim 1, wherein the gas monitoring device is a capnometer.

3. The apparatus of claim 1, wherein the exhaust portion further comprises at least one venting gas outlet for venting some or all of the gas sample from the apparatus.

4. The apparatus of claim 1, wherein the exhaust portion further comprises a pump and at least one pump gas outlet, and wherein the pump is controllably activated to draw ambient air through the exhaust line and out at least one second gas outlet, to flush the exhaust line.

5. The apparatus of claim 1, wherein the apparatus further comprises at least one auxiliary gas inlet port positioned to allow an inflow of ambient air into the apparatus when there is a negative pressure therein.

6. The apparatus of claim 1, wherein the drive mechanism comprises a motor.

7. The apparatus of claim 1, wherein the at least one gas sampling device comprises at least one thermal desorption tube.

8. The apparatus of claim 7, wherein the thermal desorption tubes are configured to enable at least nitrogen, oxygen, water, and carbon dioxide from the at least one gas sample to pass through.

9. The apparatus of claim 1, wherein the gas collection and sampling portion further comprises an ambient air component having a first ambient air intake to collect and sample ambient air from the environment.

* * * * *